(12) United States Patent
Doerr

(10) Patent No.: US 9,050,456 B2
(45) Date of Patent: Jun. 9, 2015

(54) UNIPOLAR MULTIPURPOSE ELECTRODE LINE AND STIMULATION AND DEFIBRILLATION ASSEMBLY

(75) Inventor: Thomas Doerr, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 395 days.

(21) Appl. No.: 13/539,422

(22) Filed: Jun. 30, 2012

(65) Prior Publication Data

US 2013/0023944 A1    Jan. 24, 2013

Related U.S. Application Data

(60) Provisional application No. 61/510,083, filed on Jul. 21, 2011.

(51) Int. Cl.
*A61N 1/05* (2006.01)
*A61N 1/39* (2006.01)

(52) U.S. Cl.
CPC ............. *A61N 1/0563* (2013.01); *A61N 1/3962* (2013.01)

(58) Field of Classification Search
CPC ........................... A61N 1/0563; A61N 1/3962
USPC .............................................................. 607/4
See application file for complete search history.

(56) References Cited

U.S. PATENT DOCUMENTS

| | | | |
|---|---|---|---|
| 4,103,274 A * | 7/1978 | Burgess et al. | 338/21 |
| 5,325,870 A | 7/1994 | Kroll et al. | |
| 5,336,253 A | 8/1994 | Gordon et al. | |
| 6,327,498 B1 * | 12/2001 | Kroll | 607/4 |
| 7,285,507 B2 * | 10/2007 | Fukuta et al. | 501/8 |
| 7,305,270 B1 | 12/2007 | Kroll et al. | |
| 2002/0042632 A1 | 4/2002 | Iaizzo et al. | |
| 2008/0183230 A1 | 7/2008 | Kemmetmueller et al. | |

OTHER PUBLICATIONS

European Search Report dated Nov. 5, 2012, 5 pages.

* cited by examiner

*Primary Examiner* — Mark W Bockelman
(74) *Attorney, Agent, or Firm* — ARC IP Law, PC; Joseph J. Mayo

(57) ABSTRACT

A unipolar multipurpose electrode line, comprising a line body, a unipolar plug, a defibrillation electrode attached to the line body, and a stimulation and sensing electrode, which are connected by way of a common feed line to the unipolar plug, wherein the defibrillation electrode is connected by means of at least one voltage-dependent component to the electrode feed line so that the connection has low impedance only in response to the application of a defibrillation voltage at the plug.

18 Claims, 9 Drawing Sheets

UNIPOLAR MULTIPURPOSE ELECTRODE LINE AND STIMULATION AND DEFIBRILLATION ASSEMBLY

This application claims the benefit of U.S. Provisional Patent Application 61/510,083 filed on 21 Jul. 2011, the specification of which is hereby incorporated herein by reference.

BACKGROUND OF THE INVENTION

1. Field of the Invention

At least one embodiment of the invention relates to a unipolar multipurpose electrode line.

2. Description of the Related Art

Implantable defibrillators or cardioverters (ICD) have been known for quite some time and used for clinical applications, and for decades they have been the subject of continuous technical enhancements. This applies to an even greater extent to implantable cardiac pacemakers and the related electrode lines. Combined cardiac stimulation and defibrillation assemblies, including the electrode lines (ICD electrodes) specially developed therefore, have also become established in the device market and in clinical practice as a special device category. Such combination devices are referred to as cardiac pacemakers for cardiac resynchronization therapy with defibrillators, in short CRT-D devices.

FIG. 1 shows a schematic illustration of such an assembly 100 comprising electrodes to be run into the heart H of a patient. A cardiac stimulation and defibrillation device 110 is thus connected to the heart H by way of an electrode line 120, which comprises three legs or electrode feed lines 130, 140 and 150. At or near the distal end, all legs carry sensing or stimulation electrodes (which are not individually denoted), and the leg 150 additionally carries an elongated defibrillation electrode 160. In the assembly shown, the leg 130 runs in the right atrium and the leg 140 runs in the left ventricle of the heart H, and the leg 150 carrying the defibrillation electrode 160 runs in the right ventricle (RV).

The presently available ICD electrode lines comprise a plurality of feed wires that are insulated from each other and a plurality of or multipolar plug contacts between the electrode line and the pulse generator. This makes these electrode lines expensive to produce and prone to defects. Moreover, the connection blocks of the pulse generators are large and expensive, and it is possible for users to connect the electrodes in a faulty manner. In addition, the required high voltage insulation distances within the electrode line necessitate a minimum diameter of the electrodes. Consequently installation space for shielding measures for producing MRI-compatible ICD electrodes is lost, or options of low-voltage electrodes cannot be applied to high-voltage electrodes.

BRIEF SUMMARY OF THE INVENTION

It is a feature of at least one embodiment of the invention to provide an improved electrode line of the type characterized above, which notably has a simple design, is easy to handle, and highly fit for use in practice.

The feature is achieved by a unipolar multipurpose electrode line having the characteristics as claimed herein. Moreover, an implantable stimulation and defibrillation assembly is provided, which comprises such a novel electrode line. Advantageous refinements of the inventive idea are the subject matter of the dependent claims.

The feature is implemented in one or more embodiments by effectively electrically disconnecting the defibrillation electrode of an electrode line of the type in question, when it is not in use, from the common feed line, which it shares with a stimulation and sensing electrode. At the same time, it must be ensured that, if necessary, which is to say when a shock pulse is emitted, the electrode can nonetheless become active, in this case connected to the feed line with low impedance. Finally, the feature includes the idea of connecting the defibrillation electrode by means of at least one voltage-dependent component ("switch element") to the electrode feed line so that the connection has low impedance only in response to the application of a defibrillation voltage at the plug.

It should be pointed out here that the proposed line is a non-branched or single-stranded electrode line, but it can also be a branched line, wherein in the latter case the characteristics according to at least one embodiment of the invention characterize at least one of the legs.

According to one embodiment of the invention, the switch element, or each voltage-dependent switch element is integrated in the common electrode feed line. As an alternative to, or also in combination with this embodiment, in a CRT-D system, the or at least one voltage-dependent component can be integrated in the unipolar plug connection of the stimulation and defibrillation device.

In a further embodiment of the invention, the voltage-dependent component is a varistor, notably an SiC or ZnO varistor.

According to a further embodiment, the voltage-dependent component or switch element is associated with a resistor element for forming a voltage divider so that only a very small fraction of the energy is released via the stimulation and sensing electrode when a defibrillation pulse is applied. A embodiment in which less than 5% of the energy is supplied to the stimulation and sensing electrode is preferred, with an even smaller fraction of less than 1% being even more preferred.

In a further embodiment of the invention, the defibrillation electrode is electrically segmented in the longitudinal direction, and each of the segments thereof is associated with a voltage-dependent switch element. To this end, the voltage-dependent switch elements associated with the segments are dimensioned such that a predefined voltage curve develops along the defibrillation electrode when a defibrillation pulse is emitted via the defibrillation electrode. In this way, depending on the patient-specific configuration and the spatial association between the electrode line and cardiac tissue to be stimulated present in the specific case after the implantation, it is possible to deliberately adjust a generally constant voltage over the longitudinal extension of the defibrillation electrode and an accordingly varying energy output in the individual case.

In a further embodiment of the invention, an additional stimulation electrode is inserted between two segments of the defibrillation electrode, insulated with respect to the two segments, and an additional voltage-dependent switch element is associated with this additional stimulation electrode. This embodiment enables, for example, the placement of a stimulation electrode as needed for ventricular stimulation (specifically LV stimulation) together with a shock electrode having a large overall length on a non-branched line or an individual leg of a branched line.

According to a further embodiment of the invention, the line body, at least over a part of the length thereof, comprises an insulation material having increased thermal conductivity to dissipate developing heat on the defibrillation and/or the stimulation and sensing electrodes. This embodiment enables a spatially better distributed heat transfer to the surrounding tissue in the event of heating of a feed line due to induction currents generated in a strong outer field. Because materials having increased thermal conductivity generally also have worse electrical insulation properties, this embodiment is practical specifically for the unipolar electrode line proposed here, because here highly effective electrical insulation between individual electrode feed lines is not important. In one design of the embodiment, the material having increased thermal conductivity is provided substantially over the entire longitudinal extension of the line body.

In one design embodiment of the proposed electrode line, the or at least one voltage-dependent switch element spatially directed adjoins an end of the defibrillation electrode. This can simplify the line configuration. Of course appropriate designs are also possible with the segmented defibrillation electrode mentioned above, at each end of a segment.

In a further embodiment, the switch element, or a voltage-dependent switch element is designed as a ceramic pressed or sintered body. This embodiment is particularly advantageous in conjunction with the aforementioned embodiment, and more specifically such that a cylindrical or hollow-cylindrical ceramic pressed body directly adjoins the defibrillation electrode or—in the case of a segment electrode—a press body is inserted between each individual electrode sections.

According to a further embodiment of the invention, the defibrillation electrode has a proximal extension, which is covered by an insulation material of the line body. The extension has no electrical contact with surrounding tissue, but shields a section of the electrode line running in the interior thereof. This shielding reduces the effects occurring in strong outer fields of the development of induction currents in the feed line and the occurrence of temperature peaks at electrodes having small surfaces (which is to say the sensing or stimulation electrodes), which may be potentially hazardous to the patient.

A further embodiment of the proposed electrode line is provided with at least one further sensing and/or stimulation electrode, which is connected via a separate electrode feed line. As noted above, for this purpose a separate leg may be provided, the additional electrode(s) however can also be placed on a single-stranded electrode line—in addition to the jointly connected defibrillation and sensing/stimulation electrodes. On the device side, the sensing and stimulation component of the stimulation and defibrillation device comprises at least one further output, which is connected to a further plug connection.

BRIEF DESCRIPTION OF THE DRAWINGS

Advantages and functional characteristics of the invention will additionally become apparent hereinafter from the description of exemplary embodiments based on the figures. Shown are.

DETAILED DESCRIPTION OF THE INVENTION

Figure 1:
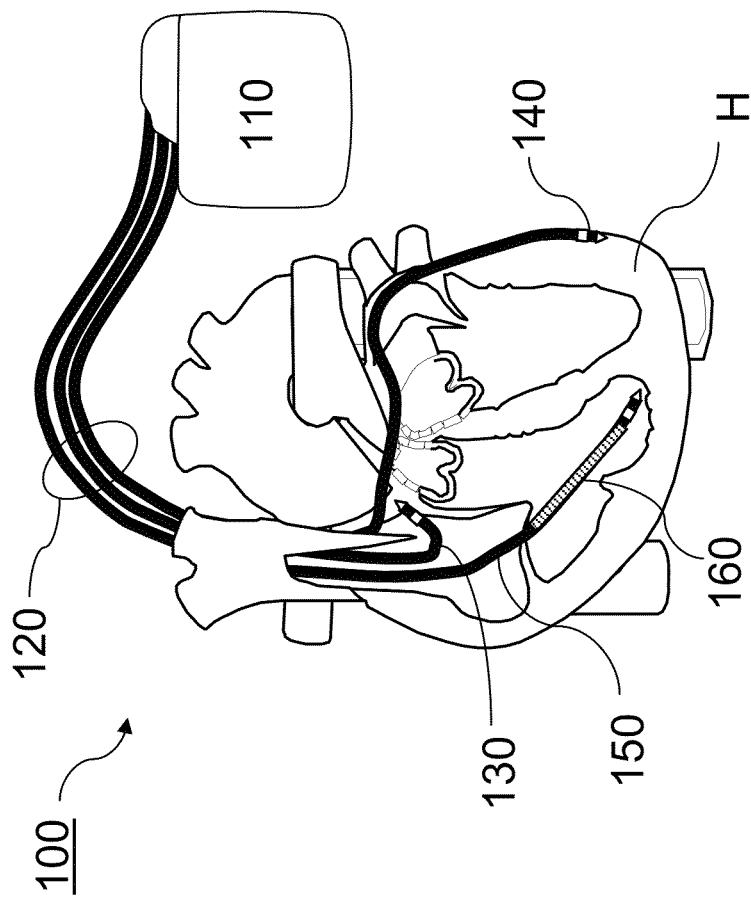
FIG. 1 is a schematic illustration of a cardiac stimulation and defibrillation assembly.
Figure 2:
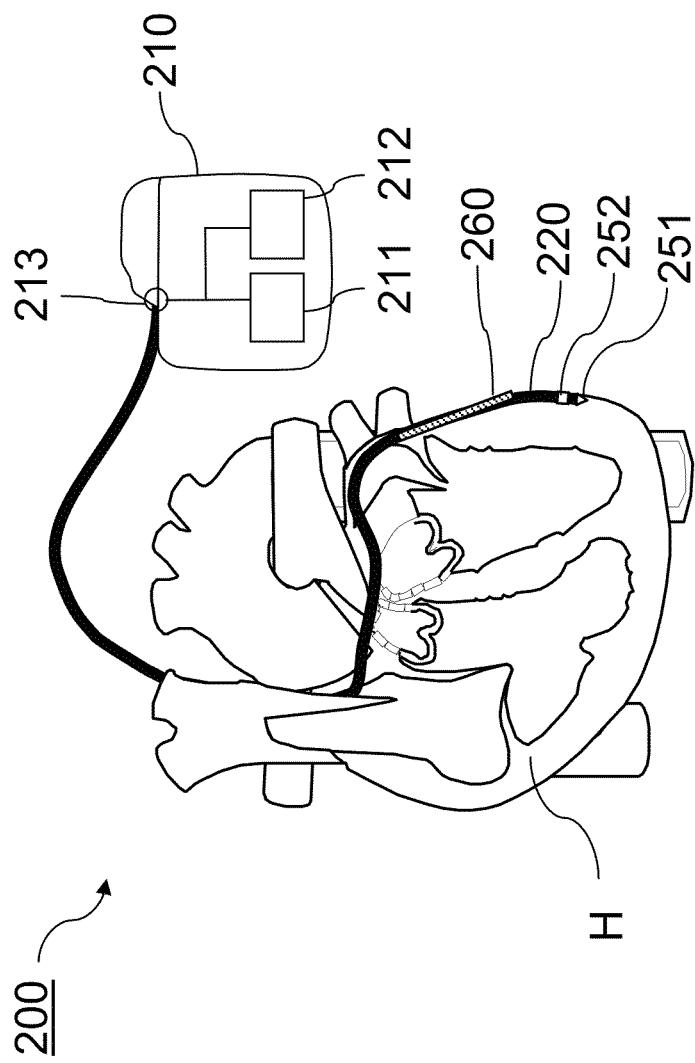
FIG. 2 is a schematic illustration of a cardiac stimulation and defibrillation assembly according to at least one embodiment of the invention.

FIG. 2 shows a cardiac stimulation and defibrillation assembly 200 connected to a heart H, which is composed of a cardiac stimulation and defibrillation device (CRT-D device) 210 and a single-stranded ICD electrode line 220. The electrode line 220 is designed as a unipolar line and at or near the distal end thereof carries a stimulation electrode 251 and a sensing electrode 252 as well as proximal thereof an elongated defibrillation electrode 260. The CRT-D device 210 contains a sensing and stimulation component 211 and a defibrillation component 212, which are both connected to a plug connection 213 for the line 220 in a unipolar manner.

This assembly is based on the assumptions that left-ventricular stimulation alone, having an accordingly adjusted AV conduction time, is not inferior to biventricular stimulation and that atrial sensing, for example via the far-field EKG, recorded between the shock coil and stimulator housing, is reliably possible. Likewise, the shown system can be employed as a conventional right-ventricular ICD system.

Figure 3:
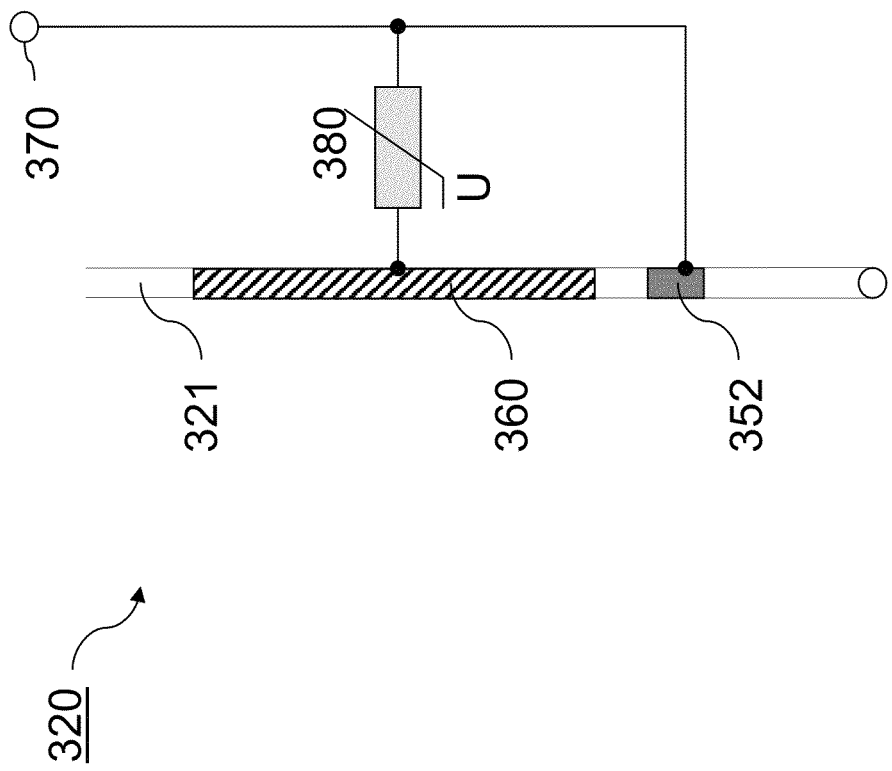
FIG. 3 is a schematic illustration to explain one embodiment of the invention, FIG. 4 are examples of characteristic varistor curves.

FIG. 3 shows schematically the end section (distal section) of a unipolar multipurpose electrode line 320 according to the invention, which near the distal end thereof carries a sensing and stimulation electrode 352 and, proximal thereof, a defibrillation electrode 360 on a line body 321. The sensing and stimulation electrode 352 and defibrillation electrode 360 share an electrode feed line 370, more specifically such that the sensing and stimulation electrode 352 is connected directly to the common feed line, and the defibrillation electrode 360 is connected to the common feed line via a varistor component 380 as the voltage-dependent switch element. In terms of the design, the varistor 380 can be configured as an integral part of the defibrillation electrode 360, or it can directly adjoin the same, or it forms part of the electrode feed line 370 in another location. An insulation of the shock coil 360 for the low-voltage application (sensing/stimulation) is established via the voltage-dependent resistor 380, and a low-impedance connection for the delivery of shocks is implemented.

So as to reduce MRI-induced electrode heating, the insulation of the line body 321 in the region proximal of the shock coil 360 is designed such that the conductivity of the insulation is increased as compared with a conventional electrode line. This is possible because the electrode comprises only a single electrical conductor on the inside, which does not need to be insulated with respect to high voltage conducting lines.

Figure 4:
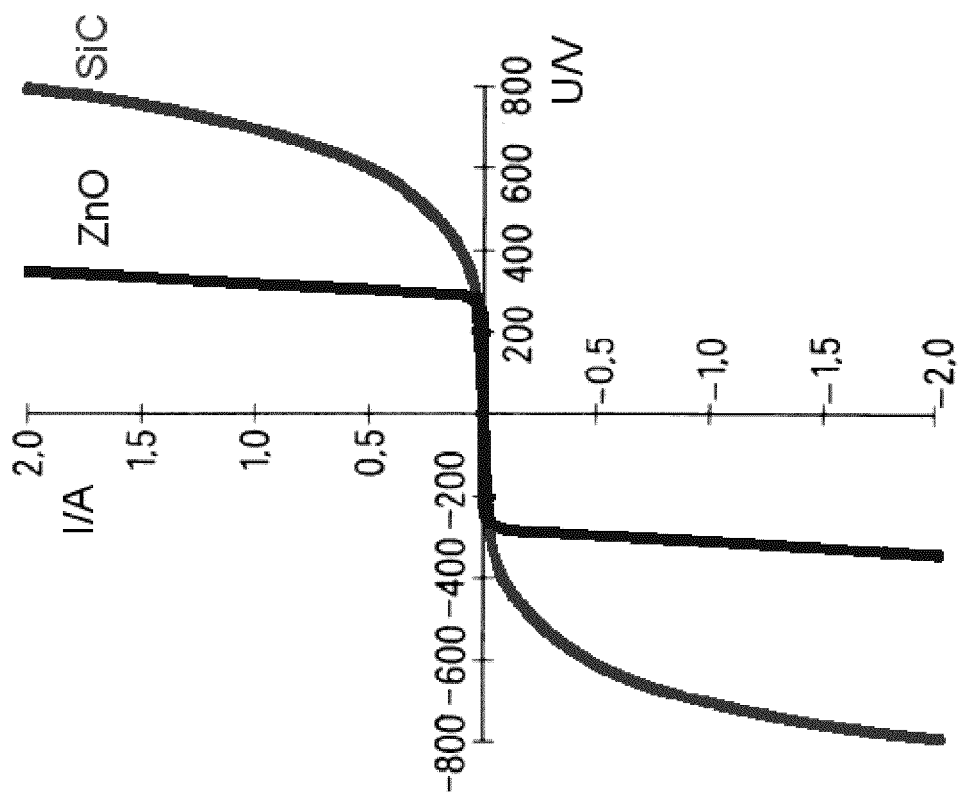

FIG. 4 shows suitable characteristic curves of typical varistors. Because varistors are not dependent on the polarity, biphasic shock delivery is possible. In addition, the voltage ranges can be adjusted very well for the defibrillation voltage range. The insulation properties at low voltages (stimulation voltages up to 10 V) are likewise ideal for the use in an electrode system. This, of course, is only shown by way of example, and other commercially available varistors having application-relevant parameters/characteristic curves can likewise be employed in the embodiment of the invention.

Figure 5:
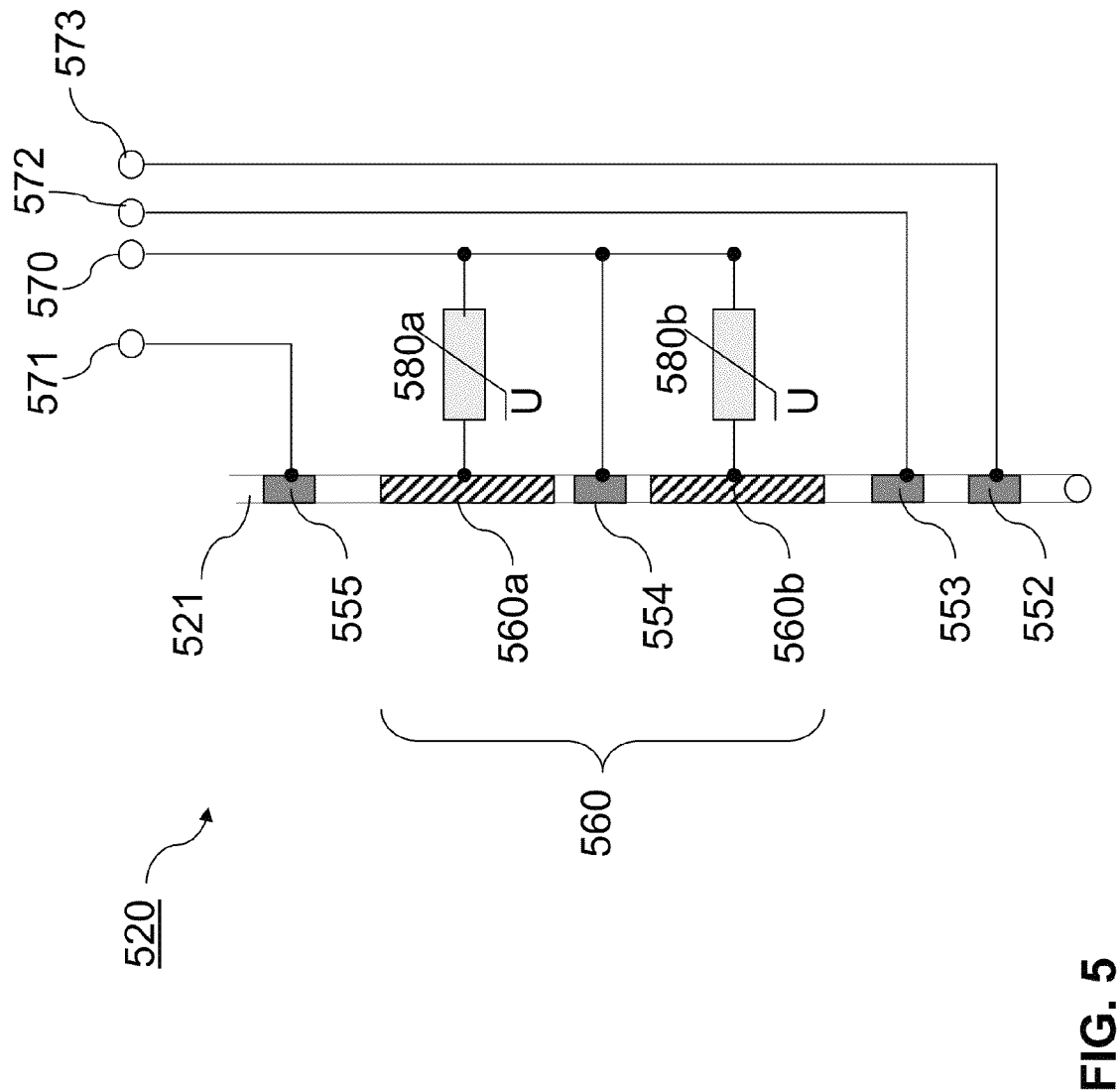
FIG. 5 is a schematic illustration to explain a further embodiment of the invention.

FIG. 5 is a more complex implementation of a single-stranded multipurpose electrode line 520 comprising a plurality of electrode feed lines as part of a single-lead CRT-D having line body 521. Here, the electrode line according to at least one embodiment of the invention comprises a 3 polar LV stimulation system 552, 553, 554, so that switching of the LV stimulation vectors is possible, whereby it is possible to adapt the stimulation site and vector to the individual patient's conditions. For the defibrillation, here two shock electrodes 560a, 560b are used, which are connected to two varistors 580a, 580b with one of the ventricular feed lines, so that geometric positioning of an LV stimulation electrode 554 below the segmented shock coil 560 is possible. Furthermore, a ring 555 is provided for the atrial stimulation and sensing. Elements 570, 571, 572 and 573 correspond to electrode feed lines, that couple with respective electrodes, wherein element 570 is the common feed line.

Such LV electrodes having 4 feed lines can already be implemented and could be connected via a single IS-4/DF-4 connection to the cardiac stimulation and defibrillation device (not shown).

Figure 6:
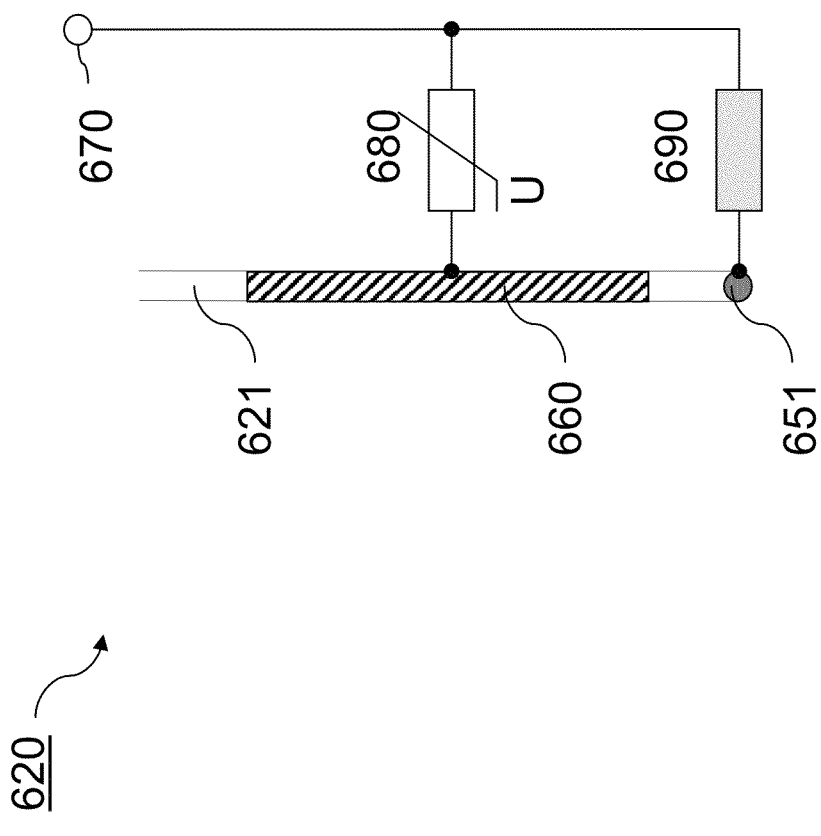
FIG. 6 is a schematic illustration to explain a further embodiment of the invention.

FIG. 6 shows an expanded design having a unipolar sensing/stimulation/shock electrode connected to an ICD/CRT system having line body 621. The electrode line 620 comprises a distal pole 651 for sensing and stimulation in the right or left ventricle, a shock coil 660 for delivering the defibrillation shock, and a single electric feed line 670, wherein this electric feed line is connected to the shock electrode 660 via a voltage-dependent component (for example a varistor or a suppressor diode) 680 and to the stimulation electrode pole 651 via a (constant) resistor 690.

The voltage-dependent resistor 680 and the constant resistor 690 form a variable voltage divider. As long as the treatment voltage is below the threshold voltage of the voltage-dependent resistor, the treatment energy is delivered almost completely to the stimulation and sensing electrode pole 651. This is the case for the stimulation.

If the treatment voltage, during the defibrillation, considerably exceeds the threshold voltage of the voltage-dependent resistor 680, a voltage divider ratio is obtained that conducts the predominant portion of treatment energy away to the shock coil 660. In this way, only very low energy conversion can take place on the small-surface-area stimulation and sensing pole 651, whereby the defibrillation treatment is implemented with low loss at the shock coil (630) and tissue damage at the stimulation electrode pole is avoided.

The divider ratio should be adjusted, for example, so that more than 99% of the defibrillation energy is delivered via the shock coil and, at the same time, the stimulation function is only impaired insignificantly. With dimensioning of the constant resistor at 500 ohm and an "on-resistance"<1 ohm of the voltage-dependent resistor during the defibrillation, and typical impedances of the electrode poles of 500 ohm for the stimulation electrode 651 and 50 ohm for the shock electrode 660, a ratio of the energy delivery of 99.5% is obtained via the shock electrode and of 0.5% via the stimulation electrode.

Figure 7:
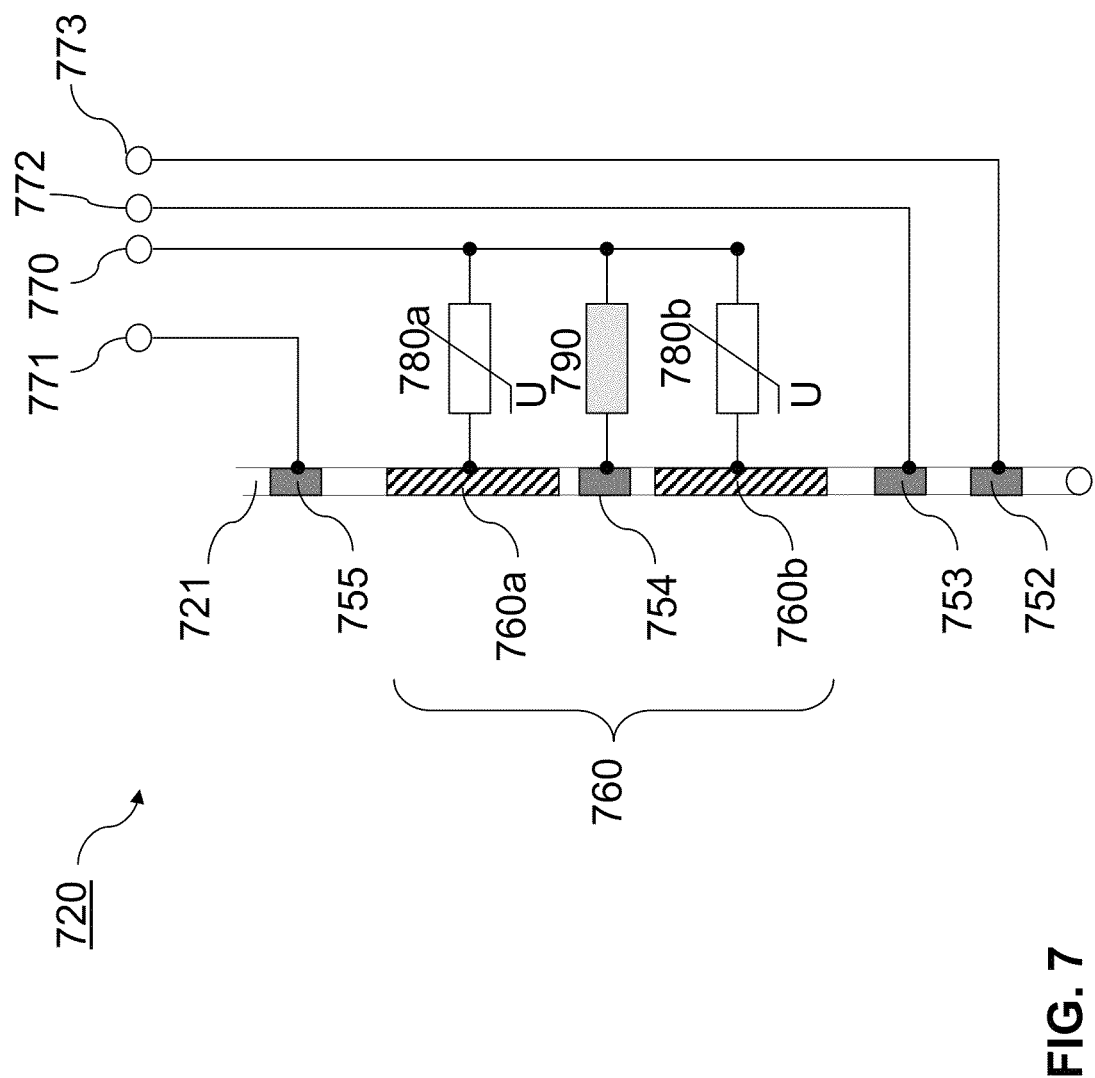
FIG. 7 is a schematic illustration to explain a further embodiment of the invention.

FIG. 7 shows a modification of the line shown in FIG. 5 and described above, comprising a plurality of electrode feed lines that couple with electrodes along line body 721 and an integrated voltage divider, as described above with reference to FIG. 6. The reference numerals denoting the parts of this electrode line 720 have been assigned based on FIG. 5, and corresponding identical or functionally equivalent parts are not described here again wherein the reference numbers are in the 700 range instead of the 500 range. Additionally provided here is the constant resistor 790, via which the LV stimulation electrode 754 placed between the segments 760a, 760b of the shock electrode 760 is connected to the common (unipolar) electrode feed line 770. The functions and effects of the voltage divider formed in this way correspond to those of the embodiment according to FIG. 6 described above.

Figure 8:
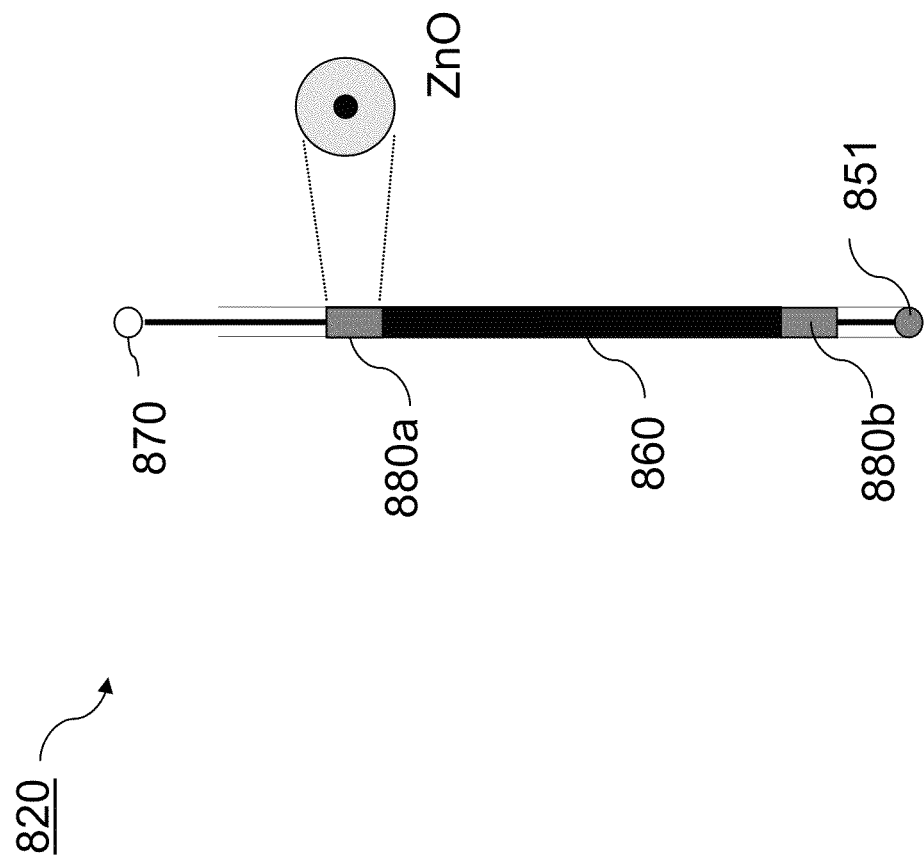
FIG. 8 is a schematic longitudinal section illustration of an electrode line according to a further embodiment of the invention.

FIG. 8 shows a possible design implementation of an electrode line according to FIG. 6. In addition here the shock coil 860 is connected with two voltage-dependent resistors 880a, 880b proximally and distally respectively to electric feed line 870 so as to optimize the electric field for the defibrillation. The voltage-dependent resistors here are preferably configured as zinc oxide sintered bodies, which are contacted to the feed line in the inside lumen. To implement the constant resistor of FIG. 6 (not shown here), the tip electrode 851 is connected, for example, using a constantan material.

Figure 9:
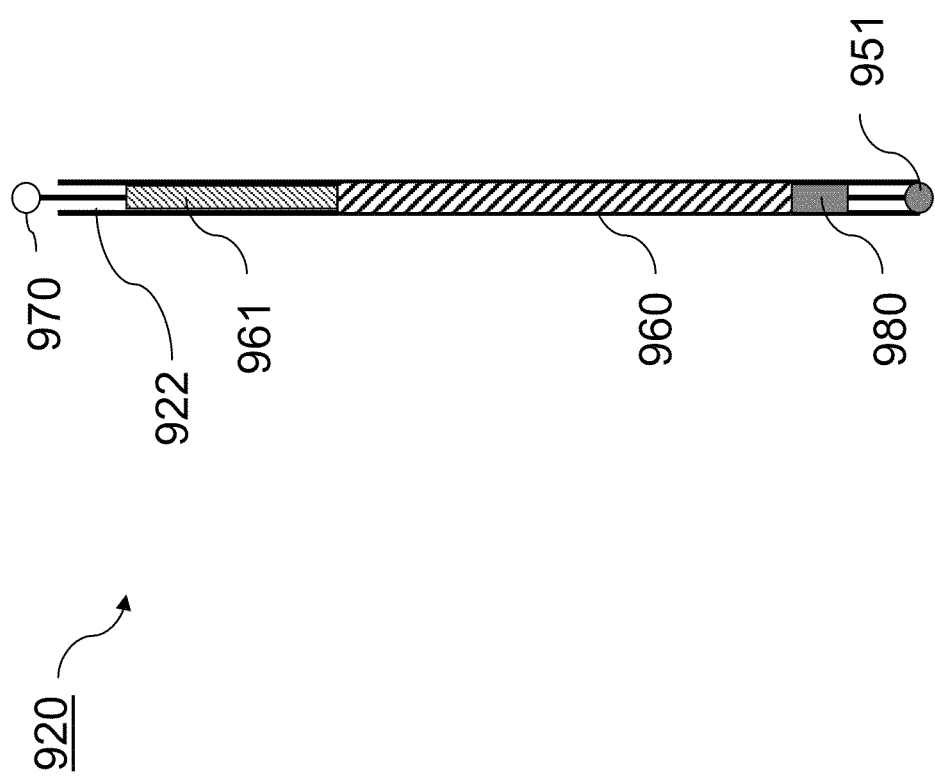
FIG. 9 is a schematic longitudinal section illustration of an electrode line according to a further embodiment of the invention.

FIG. 9 shows a further possible implementation of an electrode line according to FIG. 6. The shock coil 960 is again connected with a voltage-dependent resistor 980 to the common electrode feed line 970, which at the same time establishes the connection to the tip electrode 951.

To provide particularly effective shielding from MRI fields, the shock coil here is extended as the shield in the proximal region above the electrically necessary defibrillation electrode beneath the insulation 922 with an extension 961. In this way, a very effective and simple MRI shield is created, which can easily be accommodated in the now available installation space of the electrode line—in particular also because no high-voltage insulation requirements exist here. In addition, the insulation 922 of this electrode line 920 may also be made of a material having increased thermal conductivity—over the entire length or only in the region in which the extension 961 is located—so as to ensure, if necessary, better distributed delivery of heat developed in the conductive parts of the electrode due to interaction with the outer alternating field.

The implementation of at least one embodiment of the invention is not limited to the examples described above and concepts emphasized, but is likewise possible in a plurality of modifications, which are within the scope of standard practice in the art.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A unipolar multipurpose electrode line, comprising
a line body;
a unipolar plug coupled with said line body;
a common feed line coupled with said unipolar plug;
a stimulation and sensing electrode connected with a second feed line; and,
a defibrillation electrode attached to the line body which is connected to at least two voltage-dependent components that are connected to the common feed line, such that the connection between said common feed line and said defibrillation electrode has low impedance only in response to an application of a defibrillation voltage at the unipolar plug;
wherein the defibrillation electrode is electrically segmented in a longitudinal direction and each segment thereof is associated with a respective voltage-dependent component of said at least two voltage-dependent components, wherein each of the respective voltage-dependent components associated with the segments are dimensioned such that a predefined voltage curve develops along the defibrillation electrode when a defibrillation pulse is emitted via the defibrillation electrode, and, wherein an additional stimulation electrode is inserted between two segments of the defibrillation electrode and is connected to said common feed line.

2. The unipolar multipurpose electrode line according to claim 1, wherein the at least two voltage dependent components are integrated in the common feed line.

3. The unipolar multipurpose electrode line according to claim 1, wherein each of the at least two voltage-dependent components is a varistor, or an SiC or ZnO varistor.

4. The unipolar multipurpose electrode line according to claim 1, wherein the at least two voltage dependent components are associated with a resistor element configured to form a voltage divider such that less than 5% of the defibrillation voltage is delivered via the stimulation and sensing electrode when a defibrillation pulse is applied.

5. The unipolar multipurpose electrode line according to claim 1, wherein the at least two voltage dependent components are associated with a resistor element configured to form a voltage divider such that less than 1% of the defibrillation voltage is delivered via the stimulation and sensing electrode when a defibrillation pulse is applied.

6. The unipolar multipurpose electrode line according to claim 1, wherein the line body, at least over a part of the length thereof, comprises insulation material having increased thermal conductivity to dissipate developing heat on one or more of the defibrillation electrode segments and the additional electrode.

7. The unipolar multipurpose electrode line according to claim 6, wherein the material having increased thermal conductivity is provided substantially over an entire longitudinal extension of the line body.

8. The unipolar multipurpose electrode line according to claim 1, wherein each of the at least two voltage-dependent components spatially directly adjoins an end of the defibrillation electrode.

9. The unipolar multipurpose electrode line according to claim 1, wherein the at least two voltage dependent components are configured as a ceramic pressed or sintered body.

10. The unipolar multipurpose electrode line according to claim 1, wherein the defibrillation electrode has a proximal extension, which is covered by an insulation material of the line body, such that the extension has no electrical contact with surrounding tissue, but shields a section of the common feed line running in an interior thereof.

11. The unipolar multipurpose electrode line according to claim 1, comprising a third electrode feed line and at least one further sensing and/or stimulation electrode connected to the third electrode feed line.

12. The unipolar multipurpose electrode line according to claim 1, wherein the at least each of the at least two voltage-dependent components and the additional voltage-dependent component are switch elements.

13. The unipolar multipurpose electrode line according to claim 1, further comprising a resistor coupled with the additional stimulation electrode, wherein the resistor is further coupled with the common feed line.

14. An implantable stimulation and defibrillation assembly, comprising:
a stimulation and defibrillation device,
wherein said stimulation and defibrillation device comprises a sensing and stimulation component, a defibrillation component and a unipolar plug connection, and,
wherein the output of the defibrillation component and at least one output and an input of the sensing and stimulation component are jointly connected to said unipolar plug connection; and, a unipolar multipurpose electrode line comprising
a line body;
a unipolar plug coupled with said line body;
a common feed line coupled with said unipolar plug;
a stimulation and sensing electrode connected with a second feed line;
a defibrillation electrode attached to the line body which is connected to at least two voltage-dependent components that are connected to the common feed line, such that the connection between said common feed line and said defibrillation electrode has low impedance only in response to an application of a defibrillation voltage at the unipolar plug;
wherein the defibrillation electrode is electrically segmented in a longitudinal direction and each segment thereof is associated with a respective voltage-dependent component of said at least two voltage-dependent components, wherein each of the respective voltage-dependent components associated with the segments are dimensioned such that a predefined voltage curve develops along the defibrillation electrode when a defibrillation pulse is emitted via the defibrillation electrode, and,
wherein an additional stimulation electrode is inserted between two segments of the defibrillation electrode and is connected to said common feed line.

15. The implantable stimulation and defibrillation assembly according to claim 14, wherein the sensing and stimulation component of the stimulation and defibrillation device comprises a further plug connection and at least one further output connected to the further plug connection.

16. The implantable stimulation and defibrillation assembly according to claim 14, wherein the at least two voltage dependent components are integrated in the unipolar plug connection of the stimulation and defibrillation device.

17. The implantable stimulation and defibrillation assembly according to claim 14, wherein the at least each of the at least two voltage-dependent components and the additional voltage-dependent component are switch elements.

18. A unipolar multipurpose electrode line, comprising
a line body;
a unipolar plug coupled with said line body;
a common feed line coupled with said unipolar plug;
a stimulation and sensing electrode connected with a second feed line;
a defibrillation electrode attached to the line body which is connected to at least two voltage-dependent components that are connected to the common feed line, such that the connection between said common feed line and said defibrillation electrode has low impedance only in response to an application of a defibrillation voltage at the unipolar plug;
wherein the defibrillation electrode is electrically segmented in a longitudinal direction and each segment thereof is associated with a respective voltage-dependent component of said at least two voltage-dependent components, wherein each of the respective voltage-dependent components associated with the segments are dimensioned such that a predefined voltage curve develops along the defibrillation electrode when a defibrillation pulse is emitted via the defibrillation electrode, and,
wherein an additional stimulation electrode is inserted between the two segments of the defibrillation electrode and is connected to said common feed line;

wherein the line body, at least over a part of the length thereof, comprises insulation material having increased thermal conductivity to dissipate developing heat on one or more of the defibrillation electrode segments and the additional stimulation electrode;

wherein the material having increased thermal conductivity is provided substantially over an entire longitudinal extension of the line body; and, wherein the defibrillation electrode has a proximal extension, which is covered by an insulation material of the line body, such that the extension has no electrical contact with surrounding tissue, but shields a section of the common feed line running in an interior thereof.

* * * * *